United States Patent [19]

Bodor et al.

[11] 4,009,178

[45] * Feb. 22, 1977

[54] BROMINATING AND OXIDIZING AGENT AND METHOD OF USING SAME

[75] Inventors: Nicolae S. Bodor; James J. Kaminski, both of Lawrence, Kans.

[73] Assignee: Interx Research Corporation, Lawrence, Kans.

[ * ] Notice: The portion of the term of this patent subsequent to Jan. 6, 1993, has been disclaimed.

[22] Filed: June 16, 1975

[21] Appl. No.: 587,143

[52] U.S. Cl. .................. 260/307 C; 260/397.1; 260/397.2; 260/397.4; 260/586 R; 260/590 R; 260/593 R; 260/635 H; 260/659 R

[51] Int. Cl.² ................................ C07D 263/22

[58] Field of Search .................... 260/307 C

[56] References Cited

UNITED STATES PATENTS

| | | | |
|---|---|---|---|
| 3,465,674 | 9/1969 | Walles et al. | 102/23 |
| 3,591,601 | 7/1971 | Walles | 260/307 |
| 3,850,920 | 11/1974 | Walles | 260/247.7 J |
| 3,931,213 | 1/1976 | Kaminski et al. | 260/307 C |

Primary Examiner—Raymond V. Rush
Attorney, Agent, or Firm—Charles N. Blitzer

[57] ABSTRACT

There is provided a brominating and oxidizing agent of the formula:

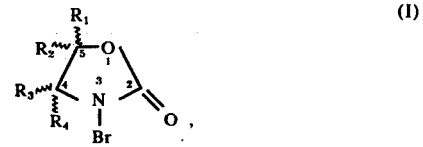

wherein $R_1$, $R_2$, $R_3$ and $R_4$ which may be the same or different, represents a member selected from the group consisting of a hydrogen atom, a $C_1$-$C_{22}$ straight or branched alkyl group, a phenyl group, and a substituted phenyl group whose substituents are selected from the group consisting of a methoxy group, a nitro group, a cyano group, a halogen atom (Br, Cl, I), a $C_1$-$C_2$ dialkylamino group, a $C_1$-$C_2$ dialkylaminomethyl group, a $C_1$-$C_2$ dialkylaminoethyl group, a $C_1$-$C_2$ dialkylammoniummethyl group, a $C_1$-$C_2$ dialkylammoniumethyl group, a $C_1$-$C_2$ trialkylammoniummethyl group, a $C_1$-$C_2$ trialkylammoniumethyl group, a $COOR_5$ group, and a $CON(R_5)_2$ group, wherein $R_5$ represents a $C_1$-$C_8$ straight or branched alkyl group.

The compounds falling within formula (I) find wide application as brominating and oxidizing agents in a number of organic reactions in which the prior art compound, N-bromosuccinimide has been employed to date. In comparison to N-bromosuccinimide, the compounds of the instant invention are characterized as being extremely stable to degradation and less polar with respect to their N-Br bond than N-bromosuccinimide such that promotion of "radical" bromine release is achieved with minimal positive bromine release.

7 Claims, No Drawings

BROMINATING AND OXIDIZING AGENT AND METHOD OF USING SAME

BACKGROUND OF THE INVENTION

1. Field of the Invention

The present invention is directed to a novel brominating and oxidizing agent and its method of application. More specifically, the present invention is directed to certain 3-bromo-2-oxazolidinones characterized as being highly stable and less polar with respect to the N-Br bond contained within the molecular structure thereof.

2. Description of the Prior Art

Walles U.S. Pat. No. 3,591,601 (patented July 6, 1971) discloses certain 3-halo-2-oxazolidinones having the formula:

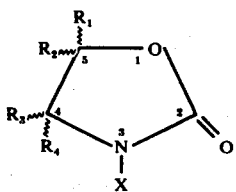

where X is broadly defined as bromine or chlorine, and $R_1$, $R_2$, $R_3$ and $R_4$ are broadly defined, inter alia, as hydrogen or lower-alkyl containing from one to four carbon atoms. The compounds are said to be useful "in germicidal, bleaching, and chemical reaction applications."

While the above definitions are broadly embracive of compounds having a quaternary carbon at the 4- and/or 5-positions of the oxazolidinone ring, i.e., compounds where either each of $R_1$, $R_2$, $R_3$ and $R_4$ is lower-alkyl or compounds where each of $R_1$ and $R_2$ or each of $R_3$ and $R_4$ is lower-alkyl (the other pair being hydrogen), such compounds are not specifically taught by Walles, who discloses only compounds where the 4- and 5-carbon atoms are either unsubstituted or where either one or both of the 4- and 5-carbon atoms bear a single lower-alkyl group. Thus, of the 2-oxazolidinones having the above general structure where each of $R_1$, $R_2$, $R_3$ and $R_4$ are either hydrogen or lower-alkyl, Walles discloses only the following species. (The "Walles Cpd. Nos." are adopted here for reference purposes hereinafter.)

| Walles Cpd. No. | $R_1$ | $R_2$ | $R_3$ | $R_4$ | X |
|---|---|---|---|---|---|
| 1 | $CH_3$ | H | H | H | Cl |
| 2 | $C_2H_5$ | H | H | H | Cl |
| 3 | H | H | H | H | Cl |
| 4 | $CH_3$ | H | H | H | Br |
| 5 | $CH_3$ | H | $CH_3$ | H | Cl |
| 6 | $C_4H_9$ | H | H | H | Br |

Certain of the above-listed Walles compounds have been prepared and it has been found that they are unstable and consequently have limited usefulness as germicidal agents. On the other hand, it has been surprisingly found that certain compounds within the ambit of the very broad disclosure of the patentee, but not specifically contemplated thereby, are suprisingly stable, in contrast with the compounds actually prepared by Walles, and possess unexpected advantageous properties as brominating and oxidizing agents.

A number of brominating agents are known to date, e.g., N-bromoacetamide, N-bromophthalimide, and N-bromosuccinimide (NBS), the latter of which is the most popular. Though, N-bromosuccinimide is usually the brominating agent of choice, this compound is quite disadvantageous from the following standpoint:

1. Firstly, it is unstable at ambient temperatures, and as such, it must be stored at temperatures ranging from 0° C or below, in order to avoid the relatively fast release of $Br_2$.

2. Secondly, although this compound has a relatively nonpolar N-Br bond, the polarity of the N-Br bond is sufficient to lead to an easy release of "positive" bromine ($Br^+$), a feature unwanted for certain bromination procedures. That is, it is more desirable in these specific bromination procedures that only "radical" bromine (Br.) be released.

3. Thirdly, from an economic standpoint, N-bromosuccinimide is quite costly to produce.

Extensive studies have shown that the polarity of the N-Br bond contained in the molecular structure of N-bromoamides and bromoimides parallels the strength of the acid from which the particular bromoamide or bromoimide is derived. Thus, it was speculated that since succinic acid is one of the weaker acids known, its corresponding bromoimide (N-bromosuccinimide) would have a relatively non-polar N-Br bond.

The present inventors have recognized that carbonic acid is a significantly weaker acid than succinic acid, and thus, its N-bromoamide or bromoimide possesses an N-Br bond of lower polarity leading to a more stable and more selective brominating and oxidizing agent.

Since it has been shown that the 5-membered ring of N-bromosuccinimide creates favorable structural conditions for most brominating reactions, the present inventor has intended to maintain the 5-membered ring structure for a useful-N-bromo compound derived from carbonic acid, i.e., the compounds of the instant invention.

From the foregoing, it is apparent that a need exists for a brominating and oxidizing agent which is substantially more stable than N-bromosuccinimide, less polar than N-bromosuccinimide with respect to the N-Br bond, and less costly from a preparatory standpoint.

SUMMARY OF THE INVENTION

It is, therefore, one object of the present invention to provide a novel brominating and oxidizing agent useful in a vast number of organic reactions for which N-bromosuccinimide has been employed in the past.

It is another object of the present invention to provide a novel brominating and oxidizing agent as described above which is more stable to degradation than N-bromosuccinimide.

Still, it is another object of the present invention to provide a novel brominating and oxidizing agent as described above which is not only more stable than N-bromosuccinimide but less polar with respect to the N-Br bond such that release of "radical" bromine is more favored than release of "positive" bromine.

Finally, it is another object of the present invention to provide a novel brominating and oxidizing agent as hereinbefore described which is commercially less expensive to produce than N-bromosuccinimide.

All of the foregoing objects are achieved with a compound having the formula:

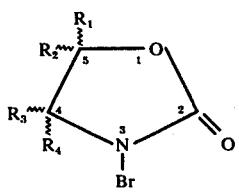

(I)

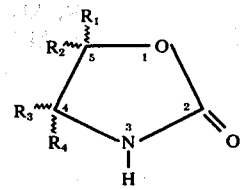

II wherein $R_1$, $R_2$, $R_3$ and $R_4$ which may be the same or different, represents a member selected from the group consisting of a hydrogen atom, a $C_1$-$C_{22}$ straight or branched alkyl group, a phenyl group, and a substituted phenyl group whose substituents are selected from the group consisting of a methoxy group, a nitro group, a cyano group, a halogen atom (Br, Cl, I), a $C_1$-$C_2$ dialkylamino group, a $C_1$-$C_2$ dialkylaminomethyl group, a $C_1$-$C_2$ dialkylaminoethyl group, a $C_1$-$C_2$ dialkylammoniummethyl group, a $C_1$-$C_2$ dialkylammoniumethyl group, a $C_1$-$C_2$ trialkylammoniummethyl group, a $C_1$-$C_2$ trialkylammoniumethyl group, a $COOR_5$ group, and a $CON(R_5)_2$ group, wherein $R_5$ represents a $C_1$-$C_8$ straight or branched alkyl group.

In the above formula (I), reference to "$C_1$-$C_2$ di and trialkylamino" and "$C_1$-$C_2$ di and trialkylammonium" denotes methyl and ethyl.

While all the compounds encompassed within formula (I) meet the objectives noted above, nevertheless, those compounds containing a substituent other than hydrogen at the 4- position ($R_3$ and $R_4$) of the molecule are preferred from the standpoint of (1) exceptional stability and (2) control of "radical" bromine release due to variations in polarity of the N-Br bond, especially the compound 3-Bromo-4,4-dimethyl-2-oxazolidinone (NBDMO).

The compounds of formula (I) are easily prepared by bromination with bromine of the corresponding unhalogenated 2-oxazolidinones having the formula:

where $R_1$, $R_2$, $R_3$ and $R_4$ have the meanings given above. The reaction is carried out in an aqueous medium and preferably at a temperature in the range from 0° C to 10° C. Although higher reaction temperatures can be used, no particular advantage is gained thereby, because the halogenated final products can be hydrolyzed by the solvent, and the rate of hydrolysis increases with increase in temperature.

Alternatively, the compounds of formula I are prepared by a transhalogenation process involving reaction of a 2oxazolidinone of formula II with an organic brominating agent, for example N-bromoacetamide, in an N-bromosuccinimide in an inert organic solvent, for example chloroform, methylene chloride or ethylene chloride. Reaction usually takes place at ambient temperature.

The unhalogenated 2-oxazolidinones of formula II are, in turn, prepared by reaction of an alkanolamine of formula III with a dilower-alkyl carbonate in the presence of a strong base, for example, an alkali metal lower-alkoxide, as represented by the reaction:

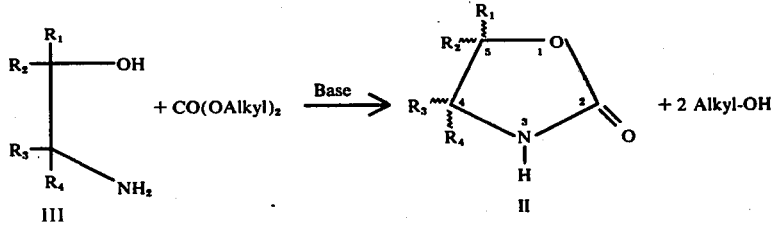

where $R_1$, $R_2$, $R_3$ and $R_4$ have the meanings given above. The reaction is carried out by heating the reactants above the boiling point of the lower-alkanol produced in the reaction, which is distilled off as it forms.

Alternatively, the compounds of formula II are prepared by reacting an alkanolamine of formula III with urea at an elevated temperature, i.e., a temperature in the range from 150°–250° C, as represented by the reaction:

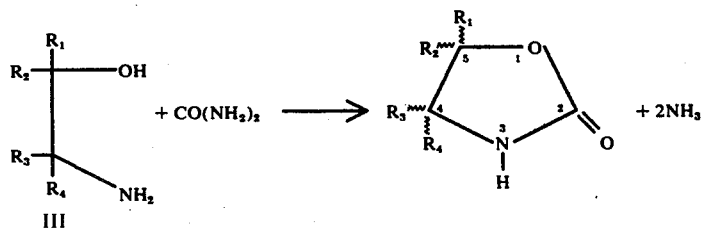

where $R_1$, $R_2$, $R_3$ and $R_4$ have the meanings give above.

The alkanolamines of formula III are a generally known class of compounds.

The unique stability of the compounds of formula (I) can be ascertained from a review of Tables "C" and "D" of applicants' co-pending application, Ser. No.

533,945, filed Dec. 18, 1974, now U.S. Pat. No. 3,931,213, covering the corresponding N-chlorinated derivatives useful as antibacterial and antifungal agents, the subject matter of which is incorporated herein be reference.

The compounds of formula (I) find wide application in a number of organic reactions requiring a brominating and/or oxidizing agent, and wherein N-bromosuccinimide has been the agent of choice in the past. Such reactions are readily known and disclosed in the following articles: L. Horner and E. H. Winkelmann, *Newer Methods of Preparative Organic Chemistry*, 3, 151 (1964) and R. Filler, *Chem. Rev.* 63, 21 (1963), respectively. In particular, the compounds of formula (I) are extremely useful in the following general organic chemical reactions requiring the presence of a brominating and/or oxidizing agent.

A. BROMINATION OF AN ALLYLIC FUNCTION:

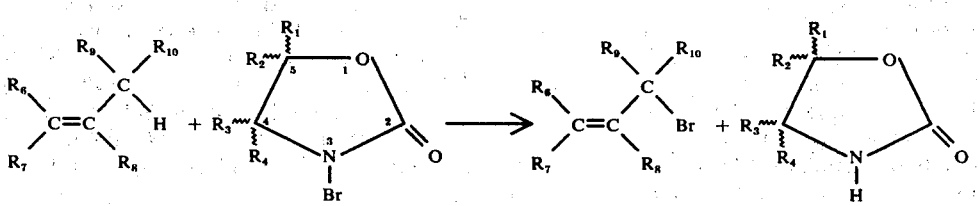

B. OXIDATION OF AN OLEFIN FUNCTION:

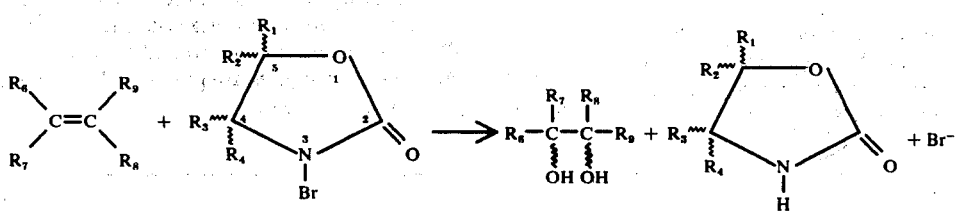

C. OXIDATION OF A SECONDARY ALCOHOL:

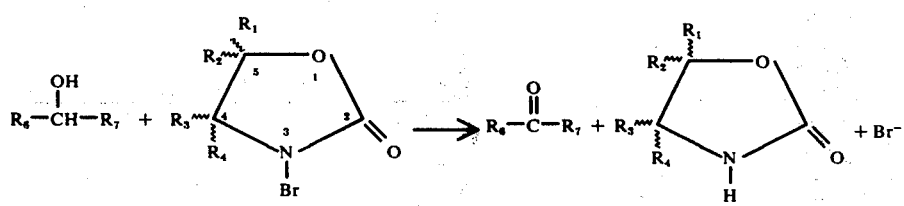

In the above reaction schemes (A) through (C) each of $R_6$-$R_{10}$ denotes any organic residual moiety which is non-reactive with NBDMO. See, the articles by Horner, et al and Filler, supra.

Without further elaboration, it is believed that one skilled in the art can, using the preceding description, utilize the instant invention to its utmost extent. The following preferred illustrative, and not limitative of the remainder of the specification and claims in any way whatsoever.

EXAMPLE I

Comparison of the Bromine Potential of N-bromosuccinimide and a Selective Compound of the Instant Application In order to demonstrate and verify the fact that the compounds of the instant application contain a less polar N-Br bond in their molecular structure than that contained in the molecular structure of N-bromosuccinimide, the "bromine potential" of each compound was determined. In this particular instance, the "bromine potential" has been defined in terms of the equilibrium constant for the reversible reaction between 3-bromo-4,4-dimethyl-2-oxazolidinone and succinimide as set out below. Reference to "DMO" denotes 4,4-dimethyl-2-oxazolidinone.

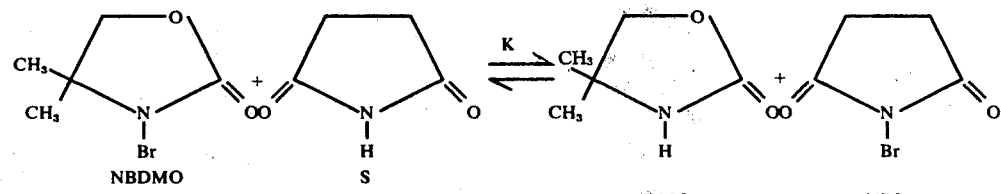

The equilibrium constant K was determined spectrophotometrically at 300 nm where 4,4-dimethyl-2-oxazolidinone and N-bromosuccinimide have no appreciable absorbance. The equilibrium constant was calculated using the equation set out below:

$$K = \frac{\left[\frac{A_e - A_o}{A_\infty - A_o}[\text{NBDMO}]_o\right]^2}{\left[\left(1 - \frac{A_e - A_o}{A_\infty - A_o}\right)[\text{NBDMO}]_o\right]\left[[S]_o - \frac{A_e - A_o}{A_\infty - A_o}[\text{NBDMO}]_o\right]}$$

where Ae has been defined as the equilibrium absorbance at 300 nm, $A_o$ is the absorbance at 300 nm for the initial concentration of 3-bromo-4,4-dimethyl-2-oxazolidinone and $A_{oo}$ has been defined as the absorbance at 300 nm assuming a total transformation of 3-bromo4,4-dimethyl-2-oxazolidinone into N-bromosuccinimide. Since the initial concentration of 3-bromo-4-,4-dimethyl-2-oxazolidinone used in the experiment did not exceed $10^{-3}$ M, $A_{oo}$ is essentially zero. The average equilibrium constant determined for the process using this procedure was $\overline{K} = 0.34$. This observation substantiates the fact that N-bromosuccinimide is a stronger "positive" bromine releasing agent relative to 3-bromo-4,4-dimethyl-2-oxazolidinone, and hence, the remaining compounds of formula (I). Consequently, the compounds of formula (I) have a less polar N-Br bond as compared to N-bromosuccinimide.

EXAMPLE II

Selective Application of the Compounds of Formula (I)

In order to demonstrate the unique applicability of the compounds of formula (I), the compound 3-bromo-4,4-dimethyl-2-oxazolidinone was prepared and employed in a number of reactions as set out below.

A. PREPARATION OF 3-BROMO-4,4-DIMETHYL-2-OXAZOLIDINONE (NBDMO):

12.3 g (0.11 mol) 4,4-dimethyl-2-oxazolidinone was dissolved in 180 ml of 1 M sodium hydroxide and the resulting solution was cooled to 0°. 19.2 g (0.012 mol) bromine was added dropwise with stirring over 0.25 hr and the reaction mixture was stirred at 0° for an additional 0.75 hr. The N-bromamine separated from the reaction mixture as an orange colored solid. The solid was isolated by filtration and thoroughly washed with cold water. Trituration of this material in petroleum ether (30°–60°) gave 16.2 g (0.084 mol), 76%, 3-bromo-4,4-dimethyl-2-oxazolidinone (NBDMO), mp 118°–120°; uv ($H_2O$) $\lambda$max 274 nm, $\epsilon = 201$ $M^{-1}$ $cm^{-1}$; ir (KBr): 2985, 1725, 1370, 1290, 1200, 1165, 1040 and 740 $cm^{-1}$; pmr ($CDCl_3$) $\delta$ 4.27 (s, 2H) and 1.33 (s, 6H) ppm.

Anal. Calcd for $C_5H_8BrNO_2$: C, 30.95; H, 4.15; N, 7.22. Found: C, 31.10; H, 4.20; N, 7.27.

The preceding example can be repeated with similar success by substituting the generically or specifically described reactants and/or operating conditions of this invention for those used in the preceding example. Thus, the following compounds are prepared by following the above-reaction scheme:

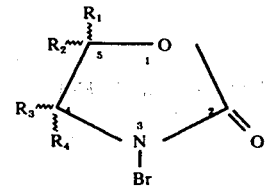

| $R_1 =$ | $R_2 =$ | $R_3 =$ | $R_4 =$ |
|---|---|---|---|
| H | H | H | H |
| $CH_3$ | $CH_3$ | H | H |
| $CH_3$ | H | $CH_3$ | H |
| H | H | $CH_3$ | $CH_3$ |
| $C_3H_7$ | $C_3H_7$ | H | H |
| $C_3H_7$ | H | $C_3H_7$ | H |
| H | H | $C_3H_7$ | $C_3H_7$ |
| $C_5H_{11}$ | $C_5H_{11}$ | H | H |
| $C_5H_{11}$ | H | $C_5H_{11}$ | H |
| H | H | $C_5H_{11}$ | $C_5H_{11}$ |
| $C_{10}H_{21}$ | $C_{10}H_{21}$ | H | H |
| $C_{10}H_{21}$ | H | $C_{10}H_{21}$ | H |
| H | H | $C_{10}H_{21}$ | $C_{10}H_{21}$ |
| $C_{15}H_{31}$ | $C_{15}H_{31}$ | H | H |
| $C_{15}H_{31}$ | H | $C_{15}H_{31}$ | H |
| H | H | $C_{15}H_{31}$ | $C_{15}H_{31}$ |
| $C_{22}H_{45}$ | $C_{22}H_{45}$ | H | H |
| $C_{22}H_{45}$ | H | $C_{22}H_{45}$ | H |
| H | H | $C_{22}H_{45}$ | $C_{22}H_{45}$ |
| Phenyl | Phenyl | H | H |
| Phenyl | H | Phenyl | H |
| H | H | Phenyl | Phenyl |
| H | H | –⟨C₆H₄⟩–OCH₃ | –⟨C₆H₄⟩–OCH₃ |
| H | H | –⟨C₆H₄⟩–NO₂ | –⟨C₆H₄⟩–NO₂ |

-continued

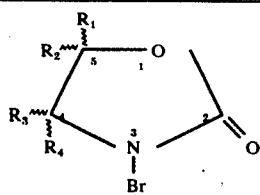

| $R_1 =$ | $R_2 =$ | $R_3 =$ | $R_4 =$ |
|---|---|---|---|
| H | H | ⟨C₆H₄⟩-CN | ⟨C₆H₄⟩-CN |
| H | H | ⟨C₆H₄⟩-Cl | ⟨C₆H₄⟩-Cl |
| H | H | ⟨C₆H₄⟩-COOCH₃ | ⟨C₆H₄⟩-COOCH₃ |
| H | H | ⟨C₆H₄⟩-COOC₅H₁₁ | ⟨C₆H₄⟩-COOC₅H₁₁ |
| H | H | ⟨C₆H₄⟩-COOC₈H₁₇ | ⟨C₆H₄⟩-COOC₈H₁₇ |
| H | H | ⟨C₆H₄⟩-CON(CH₃)₂ | ⟨C₆H₄⟩-CON(CH₃)₂ |
| H | H | ⟨C₆H₄⟩-CON(C₄H₉)₂ | ⟨C₆H₄⟩-CON(C₄H₉)₂ |
| H | H | ⟨C₆H₄⟩-CON(C₈H₁₇)₂ | ⟨C₆H₄⟩-CON(C₈H₁₇)₂ |
| ⟨C₆H₄⟩-OCH₃ | H | ⟨C₆H₄⟩-OCH₃ | H |
| ⟨C₆H₄⟩-CN | H | ⟨C₆H₄⟩-CN | H |
| ⟨C₆H₄⟩-NO₂ | H | ⟨C₆H₄⟩-NO₂ | H |
| ⟨C₆H₄⟩-Cl | H | ⟨C₆H₄⟩-Cl | H |
| ⟨C₆H₄⟩-COOC₈H₁₇ | H | ⟨C₆H₄⟩-COOC₈H₁₇ | H |
| ⟨C₆H₄⟩-CON(C₈H₁₇)₂ | H | ⟨C₆H₄⟩-CON(C₈H₁₇)₂ | H |
| CH₃ | C₅H₁₁ | H | H |
| C₂H₅ | C₁₀H₂₁ | H | H |
| C₁₀H₂₁ | H | C₁₅H₃₁ | H |
| C₂₂H₄₅ | ⟨C₆H₅⟩ | H | H |
| CH₃ | ⟨C₆H₄⟩-OCH₃ | H | H |
| H | H | ⟨C₆H₄⟩-CN | ⟨C₆H₄⟩-Cl |
| ⟨C₆H₄⟩-CON(C₅H₁₁)₂ | H | ⟨C₆H₄⟩-COOC₈H₁₇ | H |

| R₁ = | R₂ = | R₃ = | R₄ = |
|---|---|---|---|
| —⟨C₆H₄⟩—COOCH₃ | —⟨C₆H₄⟩—CON(C₈H₁₇) | H | H |
| H | $(CH_3)_2N-CH_2-$ | H | $(CH_3)_2N-CH_2-$ |
| $(CH_3)_{2+}NHCH_2-$ | H | $(CH_3)_{2+}NHCH_2-$ | H |

B. APPLICATION OF NBDMO TO THE PREPARATION OF 3-α, 12-α-DIHYDROXY-7-KETOCHOLANIC ACID:

4.30 g (0.01 mol) sodium cholate was dissolved in a solution of 2.52 g (0.03 mol) sodium bicarbonate in 80 ml of water. The solution at room temperature was treated with 2.43 g (0.013 mol) 3-bromo-4,4-dimethyl-2-oxazolidinone and the suspension was sitrred at room temperature overnite. The colorless solution was heated at 110° C for 1 hr, cooled in ice and acidified with dilute hydrochloric acid (1:2), added slowly with vigorous stirring. A white granular solid separated and after cooling in ice for 0.5 hr was collected and washed thoroughly with water. The solid was dried further by evaporation to dryness in methanol to give 3.1 g (0.0076 mol), 76%, 3-α, 12-α-dihydroxy-7-ketocholanic acid as a pale yellow solid, mp 111°-114° C (ethyl acetate); ir (KBr): 3420, 2965, 2650, 1700, 1450, 1370, 1240, 1050, and 1000 cm⁻¹; tlc (silica gel: acetone/1acetic acid): $r_f = 0.86$; mass spectrum (70 eV) m/e (rel intensity) 406 (11) and 268 (100). The melting point, infra-red spectrum and thin layer chromatogram of this material were identical to those of an authentic sample of 3-α, 12-α-dihydroxy-7-ketocholanic acid which had been prepared by the oxidation of cholic acid using N-bromosuccinimide. See, L. F. Fieser and S. Rajagopalan, *J. Amer. Chem. Soc.*, 71, 3935 (1949).

C. APPLICATION OF NBDMO TO THE PREPARATION OF 7-DEHYDROCHOLESTERYL BENZOATE:

A mixture of 2.00 g (0.004 mol) cholesteryl benzoate and 0.93 g (0.0048 mol) 3-bromo-4,4-dimethyl-2-oxazolidinone in 20 ml of hexane was refluxed for 4 minutes by the light and heat of two 75-watt reflector spot lamps placed two inches from the reaction vessel. 0.8 ml of sym-collidine was added to the boiling solution, cooled in ice and filtered to remove 4,4-dimethyl-2-oxazolidinone. The filtrate was evaporated under reduced pressure without heating to remove the hexane. An orange colored oil remained in the flask and was dissolved in 10 ml of xylene containing an additional 0.4 ml of sym-collidine. The resulting solution was heated under reflux in a nitrogen atmosphere for 15 minutes with stirring. After cooling, the sym-collidine hydrobromide which had been formed in the reaction was removed by filtration and thoroughly washed with xylene. The xylene filtrates were dried over anhydrous magnesium sulfate. Following filtration, the xylene was removed by distillation in vacuo to afford a partially crystalline yellow oil. Crystallization was complete by treatment with 50 ml of acetone, trituration for 30 minutes and cooling overnite at 0°. The solid was isolated by filtration and thoroughly washed with acetone. After drying in vacuo over calcium sulfate, 1.3 g (0.003 mol); 75%, 7dehydrocholesteryl benzoate was obtained, mp 120-122° C; uv (CHCl₃) λ 275, 285 and 297 nm; ir (KBr): 3015, 2975, 1725, 1610, 1470, 1455, 1320, 1270, 1115, 1020, 920, and 700 cm₊¹; tlc (silica gel: hexane/chloroform): $r_f = 0.90$; mass spectrum (70 eV) m/e (rel intensity) 488 (14) 366 (62) and 105 (100). The melting point, infra-red spectrum and thin layer chromatogram of this material were identical to those of the product obtained from the reaction of cholesteryl benzoate with N-bromosuccinimide. See, S. Bernstein, L. J. Binovi, L. Dorfman, K. J. Sax and Y. Subbarow, *J. Org. Chem.*, 14, 433 (1949).

Based on a spectrophotometric analysis of the products obtained, the purity and yield of the product obtained using NBDMO (75%) was better than that obtained using NBS (65%).

D. APPLICATION OF NBDMO TO THE PREPARATION OF CHOLESTANE-3-β, 5-α, 6-β-TRIOL:

A suspension of 4.5 g (0.012 mol) cholesterol in 200 ml of acetone and 25 ml of water was treated with 2.91 g (0.015 mol) 3-bromo-4,4-dimethyl-2-oxazolidinone and 2.5 ml of acetic acid. Immediately upon the addition of 3-bromo-4,4-dimethyl-2-oxazolidinone, the reaction mixture became yellow and then orange in color. In the course of one hour, the mixture became colorless and the solid all went into solution. After stirring at room temperature overnite, the solution was diluted and extracted with ether. The extracts were combined, washed with water and saturated sodium carbonate, and dried over anhydrous sodium sulfate. Following filtration, the ether was removed under reduced pressure to afford a white solid. Recrystallization from chloroform gave 1.1 g (0.003 mol), 25%, cholestane-3-β, 5-α, 6-β-triol, mp 232°-234° C, ir (KBr): 3420, 2970, 1470, 1380, 1295, 1160, 1040, 950 and 860 cm⁻¹; tlc (silica gel: acetone1% acetic acid): $r_f = 0.82$; mass spectrum (70 eV) m/e (rel intensity) 420 (3), 402 (100), 384 (100) and 366 (18). The melting point, infra-red spectrum and thin layer chromatogram of this material were identical to those of the product obtained from the reaction of cholesterol with N-bromosuccinimide. However, this product was identified as cholestane-3-β, 5-αdiol-6-one. See, L. F. Fieser and S. Rajagopalan, *J. Amer. Chem. Soc.*, 71, 3938 (1949).

E. APPLICATION OF NBDMO TO THE PREPARATION OF CHOLESTANE-3-β, 5-α-DIOL-6-ONE:

0.5 g (0.0012 mol) cholestane-3-β, 5-α, 6-β-triol was dissolved in 4.5 ml of dioxane, 0.5 ml of water and treated with 0.245 g (0.0013 mol) 3-bromo-4,4-dimethyl-2-oxazolidinone which promptly dissolved. In the course of several minutes, the color changed from yellow to orange and the reaction product began to separate. The temperature was kept at 25° by cooling and after 10 minutes the mixture was cooled in ice. The solid was isolated by filtration and washed thoroughly with 50% methanol. After extraction with ether, a second crop was obtained. Drying in vacuo over calcium sulfate gave 0.43 g (0.0010 mol), 83%, cholestane-3-β, 5-α-diol-6-one, mp 230°–231° C; ir (KBr): 3410, 2970, 1710, 1465, 1375, 1240, 1160, 1070, 1040, 1000 and 970 cm$^{-1}$; tlc (silica gel: acetone/1% acetic acid): r$_f$ = 0.92; mass spectrum (70 eV) m/e (rel intensity) 418 (100), 400 (27) and 382 (17). The yield, melting point, infra-red spectrum and thin layer chromatogram were identical to those obtained from the product of the reaction of cholestane-3-β, 5-α, 6-β-triol with N-bromosuccinimide using the procedure described by F. F. Fieser and S. Rajagoplan, *J. Amer. Chem. Soc.*, 71, 3938 (1949).

EXAMPLE III

Qualitative Stability Determination: NBDMO vs. NBS

Into separate glass vials, there was placed a quantitative sample of NBDMO (white solid material) and NBS (white solid material). Each vial was covered with a lid containing a white paper guard on the inside thereof which turns reddish-yellow in the presence of free bromine. Both vials were allowed to stand at room temperature for a period of three (3) months. At the end of the three (3) month period, each vial was opened for the purpose of examining the paper guard on the inside of the vial lid and each compound, per se.

Upon examination of the vial containing NBDMO, no decomposition was observed as evidenced by visual observance of the initial white color of the compound and the lack of any reddish-yellow color whatsoever on the paper guard maintained on the inside of the vial lid. On the other hand, visual examination of the vial containing NBS revealed a reddish-yellow compound and extreme reddish-yellow coloring on the paper guard maintained on the inside of the vial lid, both denoting release of "free" bromine.

Additional stability studies with the remaining compounds of formula (I) vs. NBS will yield essentially the same results as noted above.

From the foregoing description, one of ordinary skill in the art can easily ascertain the essential characteristics of the instant invention, and without departing from the spirit and scope thereof, can make various changes and modifications thereto to adapt it to various usages and conditions. As such, these changes and modifications are properly, equitably and intended to be, within the full range of equivalence of the following claims.

What we claim is:

1. A compound of the formula:

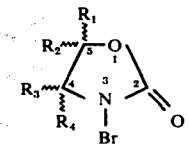

wherein R$_1$ and R$_2$ which may be the same or different, each represent a member selected from the group consisting of hydrogen and a C$_1$-C$_{22}$ straight or branched alkyl, and wherein R$_3$ and R$_4$ represent a C$_1$-C$_{22}$ straight or branched alkyl.

2. The compound of claim 1, wherein R$_1$ and R$_2$ equal H and R$_3$ and R$_4$ equal CH$_3$.

3. The compound of claim 1, wherein R$_1$ and R$_2$ equal H and R$_3$ and R$_4$ equal C$_3$H$_7$.

4. The compound of claim 1, wherein R$_1$ and R$_2$ equal H and R$_3$ and R$_4$ equal C$_5$H$_{11}$.

5. The compound of claim 1, wherein R$_1$ and R$_2$ equal H and R$_3$ and R$_4$ equal C$_{10}$H$_{21}$.

6. The compound of claim 1, wherein R$_1$ and R$_2$ equal H and R$_3$ and R$_4$ equal C$_{15}$H$_{31}$.

7. The compound of claim 1, wherein R$_1$ and R$_2$ equal H and R$_3$ and R$_4$ equal C$_{22}$H$_{45}$.

* * * * *